(12) United States Patent
Fike

(10) Patent No.: US 9,296,540 B1
(45) Date of Patent: Mar. 29, 2016

(54) SORBENT HOLDER SYSTEM FOR STORAGE OR TRANSPORT HAVING A CLEANSING ELEMENT

(71) Applicant: Randall Stuart Fike, Clarkston, MI (US)

(72) Inventor: Randall Stuart Fike, Clarkston, MI (US)

( * ) Notice: Subject to any disclaimer, the term of this patent is extended or adjusted under 35 U.S.C. 154(b) by 221 days.

(21) Appl. No.: 13/707,422

(22) Filed: Dec. 6, 2012

(51) Int. Cl.
*B65D 81/00* (2006.01)

(52) U.S. Cl.
CPC ..................................... *B65D 81/00* (2013.01)

(58) Field of Classification Search
CPC ... G01N 31/22; G01N 21/783; G01N 1/2214; G01N 1/405; G01N 33/4972; G01N 2001/2826; G01N 21/77; G01N 30/96; G01N 33/0042; G01N 1/24; B65D 17/06; B65D 1/0238; B65D 41/185; B67B 7/92; Y10T 436/25875
USPC ................. 422/86; 215/49, 226, 295
See application file for complete search history.

(56) References Cited

U.S. PATENT DOCUMENTS

| | | | |
|---|---|---|---|
| 3,933,431 A | 1/1976 | Trujillo et al. | |
| 4,071,319 A * | 1/1978 | Nugent | 422/405 |
| 4,481,297 A | 11/1984 | Zucal et al. | |
| 5,370,004 A | 12/1994 | Bossart et al. | |
| 6,186,012 B1 | 2/2001 | Kenny et al. | |
| 6,819,253 B2 | 11/2004 | Albro et al. | |
| 7,073,403 B2 | 7/2006 | Albro et al. | |
| 7,253,413 B2 | 8/2007 | Sauer et al. | |
| 7,360,461 B2 | 4/2008 | Desrochers et al. | |
| 7,566,421 B2 * | 7/2009 | Fike | 422/69 |
| 7,568,401 B1 | 8/2009 | Berends, Jr. | |
| 8,207,497 B2 | 6/2012 | Musselman | |
| 2003/0235515 A1 * | 12/2003 | Fike | 422/69 |
| 2011/0048107 A1 * | 3/2011 | Schulten et al. | 73/28.04 |

* cited by examiner

*Primary Examiner* — Sally Merkling
(74) *Attorney, Agent, or Firm* — Blank Rome LLP; Matthew J. Esserman; Aldo Noto

(57) ABSTRACT

A sorbent holder system that stores or transports a sorbent holder is provided. The sorbent holder system comprises a sorbent holder that holds sorbent material which is capable of sampling air or gas. The sorbent holder system also comprises a cleansing element which is separate from the sorbent material. The cleansing element is capable of absorbing or adsorbing at least one contaminant during storage or transportation of the sorbent holder whereby contamination of the sorbent material by the at least one contaminant is reduced or eliminated. Increased accuracy of sorbent analysis due to reduction or elimination of undesired contaminants from the sorbent during storage or transport of the sorbent holder is therefore achieved.

24 Claims, 4 Drawing Sheets

SORBENT HOLDER SYSTEM FOR STORAGE OR TRANSPORT HAVING A CLEANSING ELEMENT

FIELD OF THE INVENTION

The present invention relates generally to the field of sorbent holder sampling devices, and, more specifically, to sorbent holder systems that store or transport sorbent holders, the sorbent holder systems comprising a sorbent holder and a cleansing element.

BACKGROUND OF THE INVENTION

There is a large and continuing need for identifying and monitoring the level of pollutants (contaminants) in air and in gas streams of, for example, industrial type. This need is often addressed by obtaining a sample of the air/gas at the monitoring site and transporting the sample to a laboratory for analysis. The samples may be obtained by filling (i.e., preferably manually) a sampling holder or container such as a plastic bag, a hypodermic syringe, or an evacuated metal or glass vessel and sealing it for transportation. However, sampling devices that take a bulk air sample for transport and later analysis are often inappropriate for use in circumstances in which the contaminant being monitored is present in small concentrations, in the parts per billion or even parts per trillion range. The size of the sample that is collected is often too small for the contaminant to be detected and its concentration measured. That requirement has led to the development of air/gas sampling devices that preferentially extract and trap the contaminants from the sampled air or gas stream and hold the trapped contaminants for later release and analysis. Air/gas sampling sorbent tubes (or other similar media) are among such devices as the tube or medium contains a sorbent material that functions to extract and hold contaminants from an air/gas stream passing through the tube or over the medium. Because most contaminants of interest are organic compounds, the sorbent material (i.e. sorbents) is chosen to absorb or adsorb those compounds while allowing air/gas and inorganic compounds to pass through the tube substantially unimpeded. There exists a variety of air/gas sampling sorbent tubes or sorptive media which are used to extract and retain volatile organic compounds from air/gas flowing through them during the sampling period for later analytical determination of the volatile organic compounds contained in the air/gas. When such air/gas sampling sorbent tubes are loaded onto an analytical instrument, the retained volatile organic compounds are liberated using desorption or solvent extraction and allowed to flow into the analytical instrumentation. Analysis of the liberated volatile organic compounds is then accomplished using any of several analytical instruments and/or techniques or using a combination thereof.

The foregoing air/gas sampling sorbent tubes require that they be maintained in a contaminant-free condition prior to air/gas sampling at the monitoring site. In this regard, the air/gas sampling sorbent tube may be manufactured to have a body portion containing desired sorbent material and lateral end portions that are either capped with plastic over-caps or screw-threaded end caps. Alternatively, the air/gas sampling tube itself may be formed to be of an integral closed construction having its lateral ends or other enclosure enclosed for a later breakage by a user at a monitoring site to then expose the central body portion containing the desired sorbent material.

In the former case of capped air/gas sampling sorbent tubes or otherwise enclosed sorptive media, the capping of open sorbent tube ends or the capping of the medium may not form a perfect airtight seal and, therefore, may permit the exchange of surrounding air with the air inside the air/gas sampling tube or other sorptive medium. Any volatile or semi-volatile organic compounds contained in the air undesirably passing into the sampling tube or other sorptive medium during storage and/or transport to (and/or from) a monitoring site (or to and/or from a storage site) are adsorbed or absorbed onto the sorbent contained therein and are, during the subsequent analysis, transferred into the analytical instrument and are manifested as interferences, background, or sample overlap. Because of these deleterious analytical errors or the potential thereof, the amount of time that sampling tubes or other sorptive media can be stored prior to actual use at a sampling site is greatly reduced. In addition, the user is afforded no assurance that the sampling tube or other sorptive medium has been stored in a clean environment and is free of contamination.

Thus, it is desirable to provide a sorbent holder system which is able to overcome the above disadvantages.

Therefore, a need exists to provide a sorbent holder system that stores or transports a sorbent holder. Advantages of such a sorbent holder system would, inter alia, include the following:

Protecting the sorbent from undesired contamination during storage of the sorbent holder;

Protecting the sorbent from undesired contamination during transportation of the sorbent holder; and Enabling increased accuracy of the sorbent analysis due to reduction or elimination of undesired contaminants from the sorbent during storage or transport of the sorbent holder.

These and other advantages of the present invention will become more fully apparent from the detailed description of the invention hereinbelow.

SUMMARY OF THE INVENTION

The present invention is directed to a sorbent holder system that stores or transports a sorbent holder. The sorbent holder system comprises a sorbent holder that holds sorbent material which is capable of sampling air or gas. The sorbent holder system also comprises a cleansing element, wherein the cleansing element is separate from the sorbent material, and wherein the cleansing element is capable of absorbing or adsorbing at least one contaminant during storage or transportation of the sorbent holder whereby contamination of the sorbent material by the at least one contaminant is reduced or eliminated.

In a preferred embodiment, the sorbent holder has at least one open end which is closed via a removable closure device thereby defining an enclosed space, wherein the cleansing element is positioned within the enclosed space. The sorbent holder preferably comprises at least one porous restraining element which holds the sorbent material inside a predetermined area within the sorbent holder, wherein the at least one porous restraining element is positioned between the sorbent material and the cleansing element. The cleansing element is preferably also positioned within or in the vicinity of the removable closure device such that the cleansing element is accessible upon removal of the removable closure device. The removable closure device is preferably a removable end cap or frangible closure, wherein the cleansing element is preferably positioned within the removable end cap or frangible closure.

In another preferred embodiment, the sorbent holder is a tube having two open ends which are closed via removable closure devices thereby defining an enclosed space, wherein the cleansing element is positioned within the enclosed space. The sorbent holder preferably comprises at least two porous restraining elements which hold the sorbent material inside a predetermined area within the sorbent holder, wherein one of the at least two porous restraining elements is positioned between the sorbent material and the cleansing element. The cleansing element is preferably also positioned within or in the vicinity of at least one of the removable closure devices such that the cleansing element is accessible upon removal of the at least one of the removable closure devices. Each of the at least one of the removable closure devices is preferably a removable end cap or frangible closure, wherein the cleansing element is preferably positioned within each removable end cap or frangible closure. The sorbent holder system may optionally further comprise a container, wherein the sorbent holder and the enclosed cleansing element are contained within the container.

The sorbent holder system may further comprise a container, wherein the sorbent holder and the cleansing element are contained within the container. The cleansing element may be positioned between the sorbent holder and the container. Preferably, the container has at least one open end which is closed via a removable closure device, wherein the cleansing element may be positioned within or in the vicinity of the removable closure device such that the cleansing element is accessible upon removal of the removable closure device. The removable closure device is preferably a removable end cap or frangible closure. The cleansing element may preferably be positioned within the removable end cap or frangible closure. Alternatively, the cleansing element may preferably comprise a housing that substantially surrounds the sorbent holder. The housing may comprise a cloth-type material.

In any embodiment, the cleansing element preferably comprises a material selected from the group consisting of carbon, charcoal, activated carbon, activated charcoal, and combinations thereof.

BRIEF DESCRIPTION OF THE DRAWINGS

For the present invention to be clearly understood and readily practiced, the present invention will be described in conjunction with the following figures, wherein.

DETAILED DESCRIPTION OF THE PREFERRED EMBODIMENTS

Figure 1:
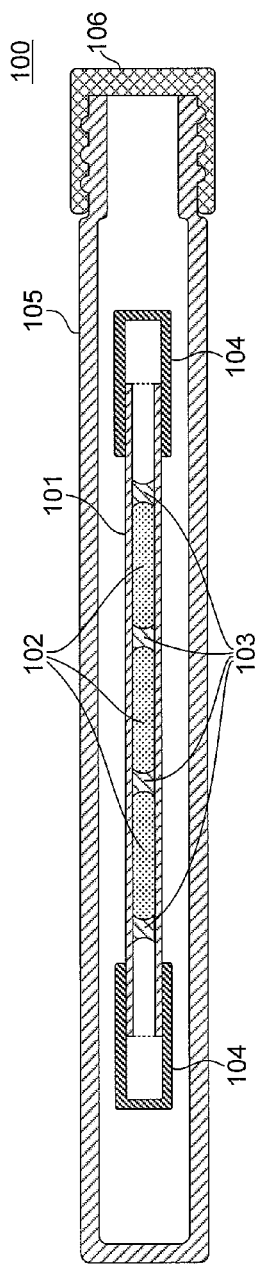
FIG. 1 is a cross-sectional side view of a prior art sorbent holder and container combination. The container contains the sorbent holder during storage or transportation of the sorbent holder.

It is to be understood that the figures and descriptions of the present invention may have been simplified to illustrate elements that are relevant for a clear understanding of the present invention, while eliminating, for purposes of clarity, other elements found in a typical sorbent holder or typical sorbent holder container. Those of ordinary skill in the art will recognize that other elements may be desirable and/or required in order to implement the present invention. However, because such elements are well known in the art, and because they do not facilitate a better understanding of the present invention, a discussion of such elements is not provided herein. It is also to be understood that the drawings included herewith only provide diagrammatic representations of the presently preferred structures of the present invention and that structures falling within the scope of the present invention may include structures different than those shown in the drawings. Reference will now be made to the drawings wherein like structures are provided with like reference designations.

Throughout this disclosure, air/gas sampling sorbent tubes (e.g., thermal desorption/sorption tubes) may alternatively be substituted by other sorptive media or sorptive devices which contain sorbent material that function to extract and hold/trap contaminants from sampled air or a gas stream encountering the sorbent material to thereby hold the trapped contaminants for later analysis. These various sorbent holding device(s) (including air/gas sampling sorbent tube(s), desorption/sorption tubes, other sorptive media, etc.) are referred to throughout this disclosure as "sorbent holder(s)".

The present invention relates generally to air or gas (air/gas) sampling sorbent holders such as a sorbent tube (or other media) designed for capturing volatile or semi-volatile organic compounds from air or a gas stream for the subsequent determination of the identity and/or quantity of the volatile or semi-volatile organic compounds contained in the air or gas stream, and particularly to a cleansing element which protects the sorbent holder or, more specifically, the sorbents contained therein and whereby the cleansing element is independent and separate from the sorbents.

The subject of this invention is an independent adsorptive or absorptive cleansing element such as a shield, insert, or element made from or containing carbon, charcoal, activated carbon, or activated charcoal that is contained in or inserted into, for example, the proximate space between an outer storage vile (i.e., container) and a sorbent holder designed to collect a sample of volatile or semi-volatile compounds from ambient or indoor air or from processes, vents, or other emissive gaseous sources. In one embodiment, the cleansing element is designed to absorb or adsorb volatile and semi-volatile organic compounds which may diffuse into the space between the container and the sorbent holder thereby preventing or retarding the absorption or adsorption of volatile or semi-volatile organic compounds by the sorbents contained within the sorbent holder contained within the container. A sorbent holder preferably includes an air/gas sampling tube made from metal, glass, or other rigid material having either open or capped ends which contains one or more sorbent materials therein. The sorbent tube is packaged in a container having dimensions sufficient to completely contain the sorbent tube. The container may comprise any material such as metal, plastic, glass, or combinations thereof, and may be sealed with glass, a lid, or other packaging which itself may preferably additionally retard contamination of the sorbents by the volatile or semi-volatile organic compounds.

FIG. 1 is a cross-sectional side view of a prior art sorbent holder and container combination 100. The container 105 contains the sorbent holder 101 during storage or transportation of the sorbent holder 101.

Figure 2:
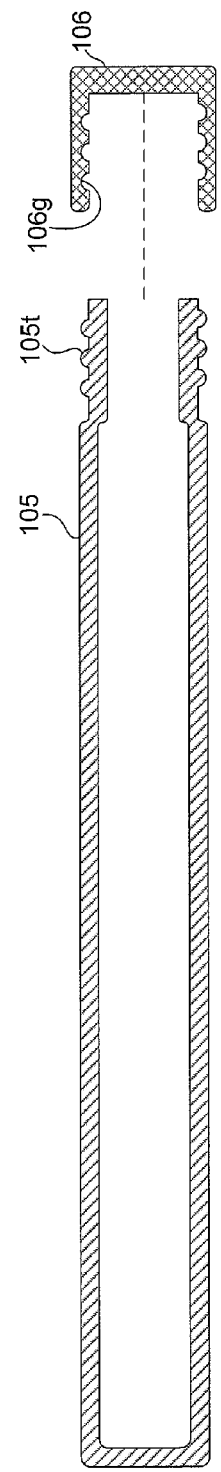
FIG. 2 is an exploded, cross-sectional side view of the container shown in FIG. 1.

FIG. 2 is an exploded, cross-sectional side view of the container 105 shown in FIG. 1.

Figure 3:
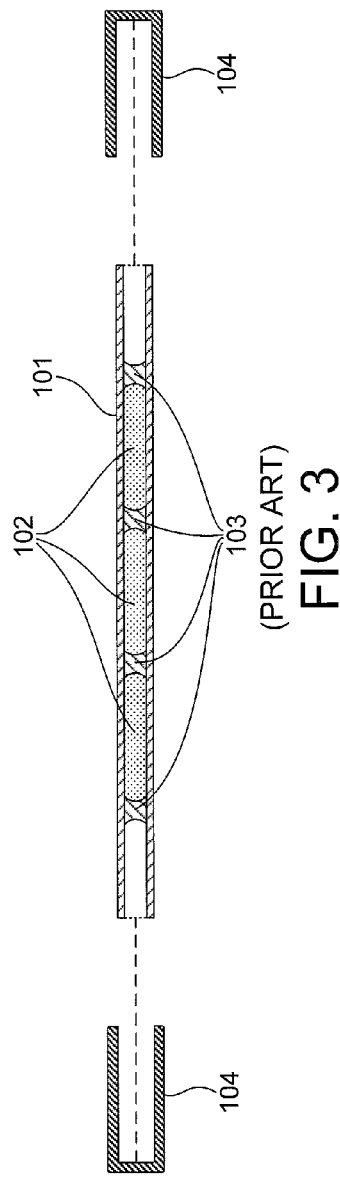
FIG. 3 is an exploded, cross-sectional side view of the sorbent holder shown in FIG. 1.

FIG. 3 is an exploded, cross-sectional side view of the sorbent holder 101 shown in FIG. 1.

Referring now to FIGS. 1-3, there is illustrated an example of a typical prior art "capped" air/gas sampling sorbent tube 101 containing one or more sorbent materials 102 separated by porous dividing elements 103 in its interior core capped at its ends with over-caps 104 and encompassed in a glass vial/container 105 which is closed using a screw-on cap 106 via a threads 105t and grooves 106g configuration (FIG. 2). The prior art "capped" air/gas sampling sorbent tube 101 includes one or more sorbent materials 102 capable of adsorbing or absorbing volatilized chemicals from a gas stream or from the air. Sorbent materials 102 may be comprised of one or more adsorbents or absorbents selected from a variety of different adsorbent or absorbent materials known in the art, which may include, for example, charcoal, Tenax®, carbon molecular sieve, Anasorb®, XAD®, silica gel, polyurethane foam, or Chromosorb®. For example, if a particular contaminant in the air is being monitored using a sorbent tube, then use of a sorbent material that is tailored to adsorbing or absorbing that particular contaminant offers advantages. However, if a user is monitoring ambient air using a sorbent tube for multiple chemical contaminants having a wide range of activities or molecular weights, then the use of several among different adsorbents or absorbents as sorbent material 102 in the air/gas sampling sorbent tube 101 provides for obtaining representative samples. The sorbent material 102 is ordinarily employed in particulate form and at an ordinary size range of 10/80 mesh. To retard the movement of the singular or composite sorbent materials 102 within the sorbent tube 101, porous dividing elements 103 which may be comprised of pressed or open glass wool or similar, non-sorptive material, may be employed. Laterally displaced from the porous dividing elements 103 is a pair of over-caps 104 suitable to cap over the open ends of the air/gas sampling sorbent tube 101. FIG. 1 illustrates a capped encompassing glass vial/container 105 as the outer enclosure. However, the outer enclosure may also be constructed of a material such as glass or plastic that forms a contiguous encapsulation. If such a configuration is utilized, the over-caps 104 may not be used. Upon removal of the sorbent tube 101 from the encompassing glass vial 105 and removal of the over-caps 104 at a desired monitoring site, the arrangement of the porous dividing elements 103 and sorbent material 102 allows a reasonably free flowing of gas/air through the air/gas sampling sorbent tube during the sampling process while at the same time ensuring an extended contact between the gas/air and the sorbent material 102.

In contradiction to the foregoing prior art air/gas sampling sorbent tube and packaging, FIGS. 4-10 are provided to illustrate possible exemplary configurations of the present invention. Many other configurations utilizing different outer enclosures such as contiguous glass or metal encapsulation, capped metal enclosures, or other configurations different from those illustrated here may be used.

Figure 4:
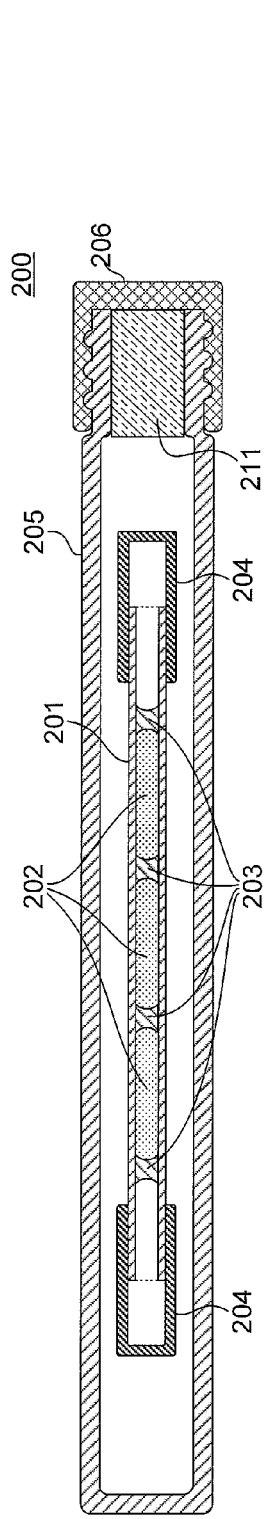
FIG. 4 is a cross-sectional side view of a sorbent holder system that stores or transports a sorbent holder, wherein the sorbent holder system comprises a sorbent holder, cleansing element, and container, and wherein the cleansing element is positioned between the sorbent holder and the container, in accordance with a preferred embodiment of the present invention.

FIG. 4 is a cross-sectional side view of a sorbent holder system 200 that stores or transports a sorbent holder 201, wherein the sorbent holder system 200 comprises a sorbent holder 201, cleansing element 211, and container 205, and wherein the cleansing element 211 is positioned between the sorbent holder 201 and the container 205, in accordance with a preferred embodiment of the present invention.

Figure 5:
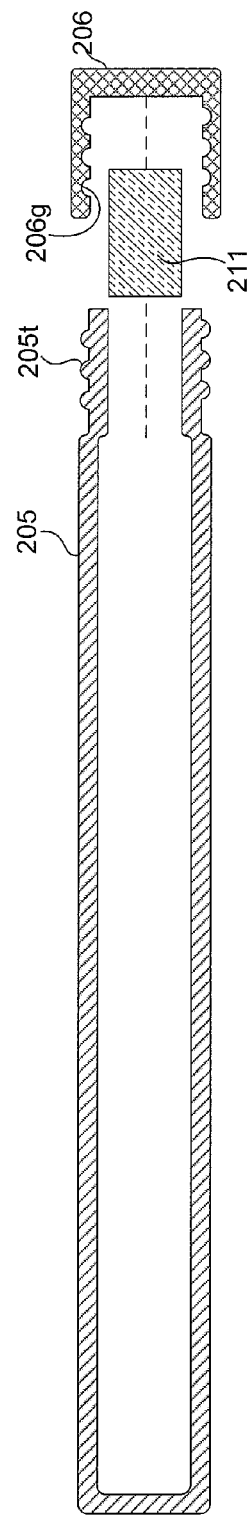
FIG. 5 is an exploded, cross-sectional side view of the cleansing element and container shown in FIG. 4.

FIG. 5 is an exploded, cross-sectional side view of the cleansing element 211 and container 205 shown in FIG. 4.

Figure 6:
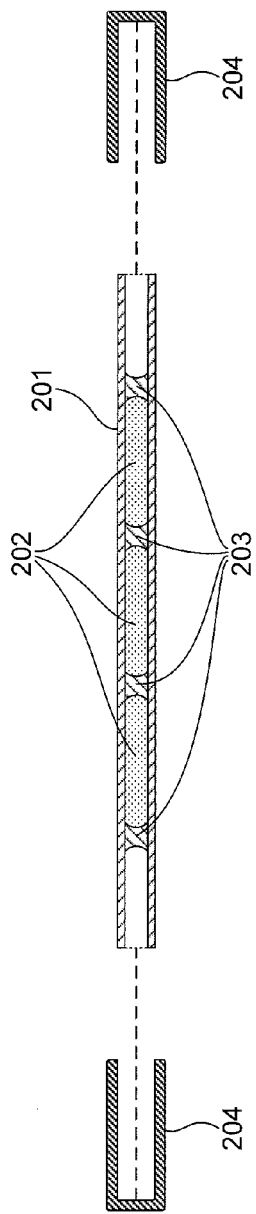
FIG. 6 is an exploded, cross-sectional side view of the sorbent holder shown in FIG. 4.

FIG. 6 is an exploded, cross-sectional side view of the sorbent holder 201 shown in FIG. 4.

FIGS. 4-6 illustrate a sorbent holder system 200. The sorbent holder system 200 includes an air/gas sampling sorbent holder 201 and a cleansing element 211 independent of the air/gas sampling sorbent holder 201. The cleansing element 211 is made from or contains carbon, charcoal, activated carbon, or activated charcoal which protects the air/gas sampling sorbent holder 201 from contaminating air entering the container 205 preferably through or near the cleansing element 211 before it contacts the sorbents 202 contained in the sorbent holder 201 thereby stripping the contaminating air of the volatile and semi-volatile contaminating chemical components contained therein. In the configuration shown in FIG. 4, the outer packaging is comprised of a vial/container 205 which is closed using a screw-on cap 206 via a threads 205t and grooves 206g configuration (FIG. 5). Depending upon the exact construction of the container, it may be beneficial to include the cleansing element as integral to the cap such as a cap liner or as an independent cleansing element 211.

Figure 7:
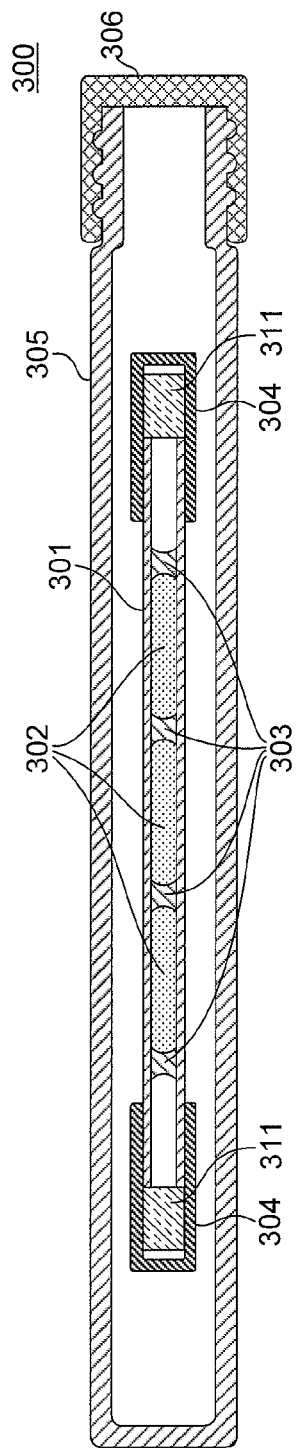
FIG. 7 is a cross-sectional side view of a sorbent holder system that stores or transports a sorbent holder, wherein the sorbent holder system comprises a sorbent holder, cleansing element, and container, and wherein the cleansing element is positioned within removable closure devices of the sorbent holder, in accordance with a preferred embodiment of the present invention.

FIG. 7 is a cross-sectional side view of a sorbent holder system 300 that stores or transports a sorbent holder 301, wherein the sorbent holder system 300 comprises a sorbent holder 301, cleansing element 311, and container 305, and wherein the cleansing element 311 is positioned within removable closure devices 304 of the sorbent holder 301, in accordance with a preferred embodiment of the present invention.

Figure 8:
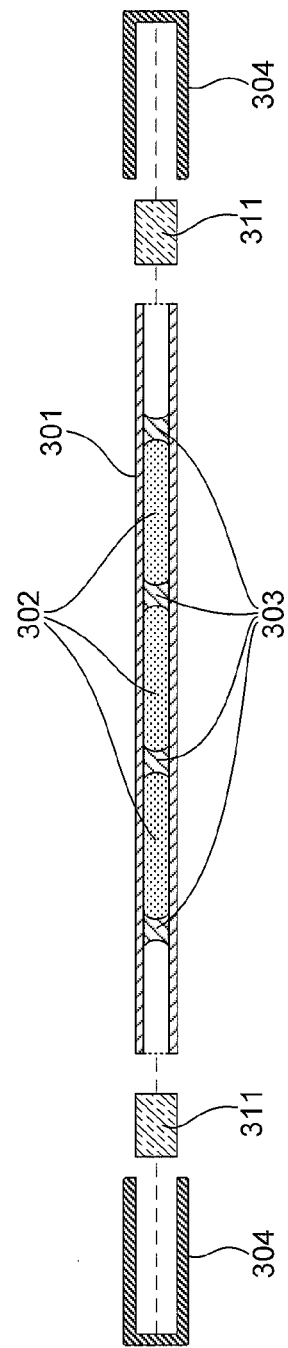
FIG. 8 is an exploded, cross-sectional side view of the sorbent holder and cleansing element shown in FIG. 7.

FIG. 8 is an exploded, cross-sectional side view of the sorbent holder 301 and cleansing element 311 shown in FIG. 7.

FIGS. 7 and 8 illustrate a sorbent holder system 300. The sorbent holder system 300 includes an air/gas sampling sorbent holder 301 and a cleansing element 311 independent from the air/gas sampling sorbent holder 301. The cleansing element 311 is made from or contains carbon, charcoal, activated carbon, or activated charcoal which protects the air/gas sampling sorbent holder 301 from contaminating air entering the container 305 and then entering the sorbent holder end caps 304 preferably through or near the cleansing element 311 before it contacts the sorbents 302 contained inside the sorbent holder 301 thereby stripping the contaminating air of the volatile and semi-volatile contaminating chemical components contained therein. In the configuration shown in FIG. 7, the outer packaging is comprised of a vial/container 305 which is closed using a screw-on cap 306 via a threads and grooves configuration. The cleansing element 311 is preferably included inside each of the pair of end-caps 304 which may be increased in length to accommodate the cleansing element 311. It may be beneficial to include the cleansing element as integral to each cap 304 such as a cap liner or as an independent cleansing element 311.

It is noted that in the embodiment of FIG. 7, container 305 including cap 306 are optional. If the container 305 including the cap 306 are omitted from sorbent holder system 300, then it would be preferable to form the sorbent holder 301 of a material with sufficient strength to withstand breakage during storage and/or transport. For example, sorbent holder 301 could be envisioned as comprising metal such as stainless steel in this or even in any embodiment throughout this disclosure.

Figure 9:
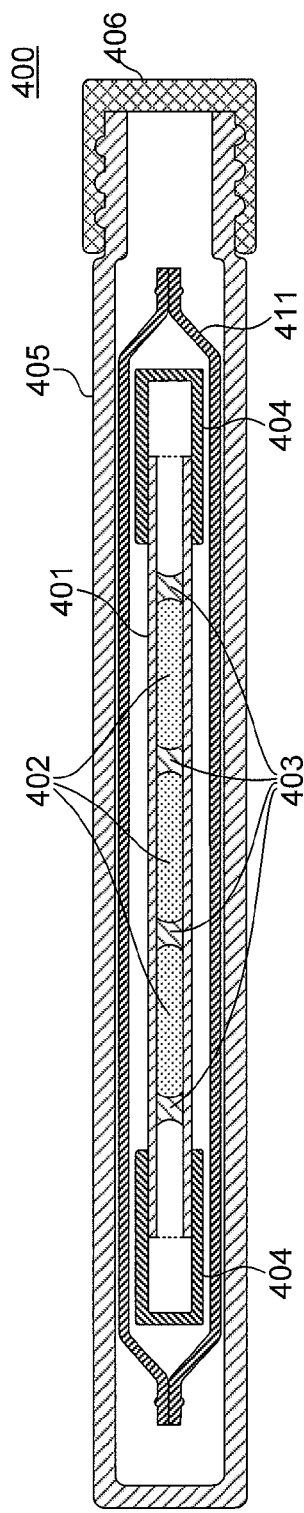
FIG. 9 is a cross-sectional side view of a sorbent holder system that stores or transports a sorbent holder, wherein the sorbent holder system comprises a sorbent holder, cleansing element, and container, wherein the cleansing element is positioned between the sorbent holder and the container, and wherein the cleansing element substantially surrounds the sorbent holder, in accordance with a preferred embodiment of the present invention.

FIG. 9 is a cross-sectional side view of a sorbent holder system 400 that stores or transports a sorbent holder 401, wherein the sorbent holder system 400 comprises a sorbent holder 401, cleansing element 411, and container 405, wherein the cleansing element 411 is positioned between the sorbent holder 401 and the container 405, and wherein the cleansing element 411 substantially surrounds the sorbent holder 401, in accordance with a preferred embodiment of the present invention.

Figure 10:
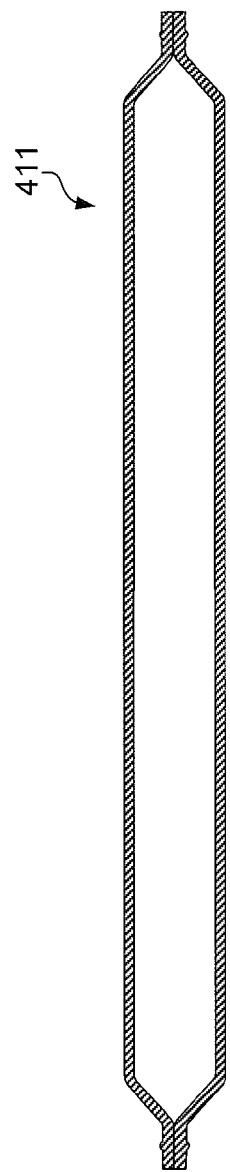
FIG. 10 is a cross-sectional side view of the cleansing element shown in FIG. 9.

FIG. 10 is a cross-sectional side view of the cleansing element 411 shown in FIG. 9.

FIGS. 9 and 10 illustrate a sorbent holder system 400. The sorbent holder system 400 includes an air/gas sampling sorbent holder 401 and a cleansing element 411 such as a carbon mesh or carbon cloth which is independent of the air/gas sampling sorbent holder 401. The cleansing element 411 is made from or contains carbon, charcoal, activated carbon, or activated charcoal which removes, absorbs, and/or adsorbs any contamination from any contaminating air entering the container 405, preferably through or near the cleansing element 411, before it contacts the sorbents 402 contained in the sorbent holder 401 thereby stripping the contaminating air of the volatile and semi-volatile contaminating chemical components contained therein. In the configuration shown in FIG. 9, the outer packaging is comprised of a vial/container 405 which is closed using a screw-on cap 406 via a threads and grooves configuration.

As per the FIG. 9 embodiment, there is provided a cleansing element which is placed over, around, or in the proximate vicinity of a sorbent holder. The cleansing element comprises carbon, charcoal, activated carbon, or activated charcoal that is proximate to, but may not entirely envelop, a sorbent holder which is designed to collect a sample of volatile or semi-volatile compounds from ambient or indoor air or from processes, vents, or other emissive gaseous sources. The cleansing element is independent of and separate from the sorbent holder or is either independent of and separate from an outer enclosure/container or an integral part of the container, the cleansing element having design and dimensions sufficient to be contained within the space between the air/gas sampling sorbent holder therein and the container. The cleansing element serves as a shield between possible ingress and/or entraining of surrounding air and the sorbent holder. The use of the cleansing element may also provide a cushioning element to reduce contact between the sorbent holder and the container thereby reducing the possibility of breakage of the sorbent holder and the container during storage or transport. The shield may optionally be held in place (and for possibly maintaining its shape) during storage or transport via, for example, a tie or strap. The optional tie or strap may comprise any material such as metal, glass, plastic, or combinations thereof. Further, the sorbent holder may be removed from the container with the certainty that the internal sorbent material of the air/gas sampling holder has not been prematurely exposed to pre-monitoring site air or gases during the prolonged period encompassing storage, handling, or transport.

The present invention is directed to a sorbent holder system 100, 200, 300, 400 that stores or transports a sorbent holder 101, 201, 301, 401. The sorbent holder system 100, 200, 300, 400 comprises a sorbent holder 101, 201, 301, 401 that holds sorbent material 102, 202, 302, 402 which is capable of sampling air or gas. The sorbent holder system 100, 200, 300, 400 also comprises a cleansing element 111, 211, 311, 411, wherein the cleansing element 111, 211, 311, 411 is separate from the sorbent material 102, 202, 302, 402, and wherein the cleansing element 111, 211, 311, 411 is capable of absorbing or adsorbing at least one contaminant during storage or transportation of the sorbent holder 101, 201, 301, 401 whereby contamination of the sorbent material 102, 202, 302, 402 by the at least one contaminant is reduced or eliminated.

In a preferred embodiment which may be the type shown in FIG. 7, the sorbent holder 301 has at least one open end which is closed via a removable closure device thereby defining an enclosed space, wherein the cleansing element 311 is positioned within the enclosed space. The sorbent holder 301 preferably comprises at least one porous restraining element 303 which holds the sorbent material 302 inside a predetermined area within the sorbent holder 301, wherein the at least one porous restraining element 303 is positioned between the sorbent material 302 and the cleansing element 311. The cleansing element 311 is preferably also positioned within or in the vicinity of the removable closure device such that the cleansing element 311 is accessible upon removal of the removable closure device. The removable closure device is preferably a removable end cap 304 or frangible closure, wherein the cleansing element 311 is preferably positioned within the removable end cap 304 or frangible closure.

In another preferred embodiment (again, which may be the type as per FIG. 7), the sorbent holder 301 is a tube having two open ends which are closed via removable closure devices thereby defining an enclosed space, wherein the cleansing element 311 is positioned within the enclosed space. The sorbent holder 301 preferably comprises at least two porous restraining elements 303 which hold the sorbent material 302 inside a predetermined area within the sorbent holder 301, wherein one of the at least two porous restraining elements 303 is positioned between the sorbent material 302 and the cleansing element 311. The cleansing element 311 is preferably also positioned within or in the vicinity of at least one of the removable closure devices such that the cleansing element 311 is accessible upon removal of the at least one of the removable closure devices. Each of the at least one of the removable closure devices is preferably a removable end cap 304 or frangible closure, wherein the cleansing element 311 is preferably positioned within each removable end cap 304 or frangible closure. The sorbent holder system 300 may optionally further comprise a container 305, wherein the sorbent holder 301 and the enclosed cleansing element 311 are contained within the container 305.

The sorbent holder system 200, 300, 400 may further comprise a container 205, 305, 405 as per, for example, FIGS. 4, 7, and 9, respectively, wherein the sorbent holder 201, 301, 401 and the cleansing element 211, 311, 411 are contained within the container 205, 305, 405. As per FIGS. 4 and 9, respectively, the cleansing element 211, 411 is positioned between the sorbent holder 201, 401 and the container 205, 405. Preferably, the container 205, 405 has at least one open end which is closed via a removable closure device, wherein the cleansing element 211, 411 is positioned within or in the vicinity of the removable closure device such that the cleansing element 211, 411 is accessible upon removal of the removable closure device. The removable closure device is preferably a removable end cap 206, 406 or frangible closure. The cleansing element 211 in FIG. 4 is preferably positioned within the removable end cap 206 or frangible closure. The cleansing element 411 in FIG. 9 preferably comprises a housing that substantially surrounds the sorbent holder 401. The housing may comprise a cloth-type material.

In any embodiment, the cleansing element preferably comprises a material selected from the group consisting of carbon, charcoal, activated carbon, activated charcoal, and combinations thereof. The cleansing element may alternatively comprise other materials which function to absorb or adsorb contaminants prior to sampling (i.e., during storage and/or transport) such as carbon molecular sieve or Tenax®. The cleansing element in the embodiments of FIGS. 4 and 7, for example, may take any form such as a coil, plug, insert, sponge, powder, cloth, particulate, packet, or colloid.

In embodiments including the container with a frangible closure as the removable closure device, the frangible closure may be of the type disclosed in U.S. Pat. No. 7,566,421 (issued to Fike) with reference to frangible element 60 of encapsulation element 44, for example. The frangible closure for the container may be integral with the container or may be formed of a different material.

In embodiments including the sorbent holder with a frangible closure as the removable closure device, the frangible closure may be similar to the type disclosed in U.S. Pat. No. 7,566,421 with reference to frangible element 60 of encapsulation element 44, for example. The frangible closure for the sorbent holder may be integral with the sorbent holder or may be formed of a different material.

In any embodiment, the sorbent holder may be of the types disclosed in U.S. Pat. No. 7,566,421 with reference to "sampling sorbent tube 42", for example. The sorbent holder may comprise metal, glass, plastic, or combinations thereof.

In any embodiment, the sampled air may be any type of air such as ambient air or indoor air. The sampled gas may be any type of gas such as from processes, vents, or other emissive gaseous sources. Examples of types of air or gas to be sampled in any embodiment are disclosed in U.S. Pat. No. 7,566,421.

In any embodiment, the sorbents may be any type of absorbent or adsorbent material, and may preferably be solid. Examples of types of sorbents to be used in any embodiment are disclosed in U.S. Pat. No. 7,566,421. The sorbent(s) may comprise either a single absorbent/adsorbent or a plurality of absorbents/adsorbents of the same or different sizes, weights, and/or types. The sorbents are preferably in particulate form at a size range of 10/80 mesh. The sorbents are disposed within the sorbent holder for collection and/or absorbing/adsorbing of volatile and/or semi-volatile chemicals from air or gas.

In any embodiment, the container may be of the types disclosed in U.S. Pat. No. 7,566,421 with reference to encapsulation element 44, for example. The container may comprise any material such as metal, plastic, glass, or combinations thereof.

In any embodiment, the removable closure device may comprise an end cap (e.g., screw-type, snap or slip-on), lid (e.g., screw-type, snap or slip-on), frangible closure, plug (e.g., screw-type or non screw-type insert), or combinations thereof. The removable closure device may comprise any material such as metal, plastic, glass, or combinations thereof. Caps for the sorbent holder may be of the type disclosed in U.S. Pat. No. 7,566,421 with reference to prior art "over-caps 18", for example.

The present invention as per any of the embodiments/techniques throughout this disclosure maintain cleanliness of sorbent holders through an active process via presence of the cleansing element. Whereas, current methods for maintaining cleanliness of sorbent holders rely on passive techniques, i.e. they simply restrict in ingress and/or entrainment of potentially contaminated air, and are, therefore, less effective than any of the techniques of the present invention. The present invention thusly provides the most effective way of maintaining the cleanliness of sorbent holders prior to sampling (i.e., during storage and/or transport).

The dimensions, size, and shape of any component within the sorbent holder system 100, 200, 300, 400 such as the sorbent holder, cleansing element, and/or container may differ than that described in the exemplary embodiments above. Such differences are considered to be within the scope of the present invention.

The contemplated modifications and variations specifically mentioned above and below are considered to be within the spirit and scope of the present invention.

Those of ordinary skill in the art will recognize that various modifications and variations may be made to the embodiments described above without departing from the spirit and scope of the present invention. For example, although the sorbent holder 101, 201, 301, 401 is described above as including four dividers 103, 203, 303, 403 which contain three separate areas where sorbents 102, 202, 302, 402 reside, any number of sorbent areas and corresponding dividers may alternatively be employed in accordance with the present invention. It is therefore to be understood that the present invention is not limited to the particular embodiments disclosed above, but it is intended to cover such modifications and variations as defined by the following claims.

What is claimed is:

1. A sorbent holder system that stores or transports a sorbent holder, the sorbent holder system comprising:
   a sorbent holder that holds sorbent material which is capable of sampling air or gas, wherein the sorbent holder comprises:
   a tube; and
   at least one porous restraining element positioned within the tube; and
   a cleansing element positioned outside the tube, wherein the cleansing element is separate from the sorbent material, wherein the cleansing element is capable of absorbing or adsorbing at least one contaminant during storage or transportation of the sorbent holder whereby contamination of the sorbent material by the at least one contaminant is reduced or eliminated.

2. The sorbent holder system of claim 1, wherein the tube has at least one open end which is closed via a removable closure device thereby defining an enclosed space, and wherein the cleansing element is positioned within the enclosed space.

3. The sorbent holder system of claim 2, wherein the at least one porous restraining element holds the sorbent material inside a predetermined area within the tube, wherein one of the at least one porous restraining element is the porous restraining element closest to the removable closure device and is positioned between the sorbent material and the cleansing element, and wherein the enclosed space extends from the removable closure device to the one of the at least one porous restraining element.

4. The sorbent holder system of claim 2, wherein the cleansing element is also positioned within or in the vicinity of the removable closure device such that the cleansing element is accessible upon removal of the removable closure device.

5. The sorbent holder system of claim 2, wherein the removable closure device is a removable end cap or frangible closure, and wherein the cleansing element is positioned within the removable end cap or frangible closure.

6. The sorbent holder system of claim 1, wherein the tube includes two open ends which are closed via removable closure devices thereby defining an enclosed space, and wherein the cleansing element is positioned within the enclosed space.

7. The sorbent holder system of claim 6, wherein the at least two porous restraining elements hold the sorbent material inside a predetermined area within the tube, wherein one of the at least two porous restraining elements is the porous restraining element closest to one of the removable closure devices and is positioned between the sorbent material and the cleansing element, and wherein the enclosed space extends from the one removable closure device to the one of the at least two porous restraining elements.

8. The sorbent holder system of claim 6, wherein the cleansing element is also positioned within or in the vicinity of at least one of the removable closure devices such that the cleansing element is accessible upon removal of the at least one of the removable closure devices.

9. The sorbent holder system of claim 6, wherein each of the removable closure devices is a removable end cap or frangible closure, and wherein the cleansing element is positioned within each removable end cap or frangible closure.

10. The sorbent holder system of claim 6 further comprising a container, wherein the sorbent holder and the enclosed cleansing element are contained within the container.

11. The sorbent holder system of claim 1 further comprising a container, wherein the sorbent holder and the cleansing element are contained within the container, and wherein the cleansing element is positioned between the sorbent holder and the container.

12. The sorbent holder system of claim 11, wherein the container has at least one open end which is closed via a removable closure device, and wherein the cleansing element is positioned within or in the vicinity of the removable closure device such that the cleansing element is accessible upon removal of the removable closure device.

13. The sorbent holder system of claim 12, wherein the removable closure device is a removable end cap or frangible closure, and wherein the cleansing element is positioned within the removable end cap or frangible closure.

14. The sorbent holder system of claim 11, wherein the cleansing element comprises a housing that substantially surrounds the sorbent holder.

15. The sorbent holder system of claim 14, wherein the housing comprises a cloth-type material.

16. The sorbent holder system of claim 1, wherein the cleansing element comprises a material selected from the group consisting of carbon, charcoal, activated carbon, activated charcoal, and combinations thereof.

17. The sorbent holder system of claim 2, wherein the removable closure device is a removable end cap, and wherein the cleansing element is positioned within the removable end cap and is removable with the removable end cap upon removal of the removable end cap from the tube.

18. The sorbent holder system of claim 6, wherein each of the removable closure devices is a removable end cap, and wherein the cleansing element is positioned within each removable end cap and is removable with each removable end cap upon removal of each removable end cap from the tube.

19. The sorbent holder system of claim 11, wherein the container has at least one open end which is closed via a removable closure device, and wherein the cleansing element is positioned between the removable closure device and an end of the tube closest to the removable closure device.

20. The sorbent holder system of claim 12, wherein the removable closure device is a removable end cap, and wherein the cleansing element is positioned within the removable end cap.

21. A sorbent holder system that stores or transports a sorbent holder, the sorbent holder system comprising:
   a sorbent holder that holds sorbent material which is capable of sampling air or gas, wherein the sorbent holder comprises:
      a tube; and
      at least one porous restraining element positioned within the tube; and
   a cleansing element, wherein the cleansing element is separate from the sorbent material, wherein the cleansing element is capable of absorbing or adsorbing at least one contaminant during storage or transportation of the sorbent holder whereby contamination of the sorbent material by the at least one contaminant is reduced or eliminated;
   wherein the tube has at least one open end which is closed via a removable end cap, and wherein the cleansing element is positioned within the removable end cap and is removable with the removable end cap upon removal of the removable end cap from the tube.

22. The sorbent holder system of claim 21, wherein the tube has a first end and a second end, wherein the sorbent holder comprises at least two porous restraining elements which hold the sorbent material inside a predetermined area within the tube, wherein one of the at least two porous restraining elements is the porous restraining element closest to the first end or the second end and is positioned between the sorbent material and the cleansing element, and wherein the cleansing element is positioned within the tube between the one of the at least two porous restraining elements and either the first end or the second end that is closest to the one of the at least two porous restraining elements.

23. The sorbent holder system of claim 21, wherein the tube has at least one end, wherein the at least one porous restraining element holds the sorbent material inside a predetermined area within the tube, wherein one of the at least one porous restraining element is the porous restraining element closest to one of the at least one end and is positioned between the sorbent material and the cleansing element, and wherein the cleansing element is positioned between the one of the at least one porous restraining element and the one of the at least one end.

24. The sorbent holder system of claim 21, wherein the cleansing element is positioned outside the tube.

* * * * *